(12) United States Patent
Girardi et al.

(10) Patent No.: US 6,924,406 B2
(45) Date of Patent: Aug. 2, 2005

(54) PROCESS FOR SEPARATING MIXTURES OF HYDROCARBON ISOMERS IN GAS PHASE ON MOLECULAR SIEVES

(75) Inventors: Gianluca Girardi, San Donato Milanese (IT); Gianni Pandolfi, Novara (IT); Renzo Bignazzi, Legnano (IT); Renato Paludetto, Milan (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/886,994

(22) Filed: Jun. 25, 2001

(65) Prior Publication Data

US 2002/0062056 A1 May 23, 2002

(30) Foreign Application Priority Data

Jun. 29, 2000 (IT) ..................................... MI2000A1458

(51) Int. Cl.[7] ................................................ C07C 7/12
(52) U.S. Cl. ...................... 585/822; 585/820; 585/825; 585/826; 585/827; 585/828; 585/829; 585/831
(58) Field of Search .................................. 585/820–831

(56) References Cited

U.S. PATENT DOCUMENTS 5,863,315 A * 1/1999 Jullian et al. ............... 585/829

FOREIGN PATENT DOCUMENTS

| EP | 0 820 972 | 1/1998 |
|---|---|---|
| FR | 2 773 149 | 7/1999 |

* cited by examiner

Primary Examiner—Walter D. Griffin
Assistant Examiner—Tam M. Nguyen
(74) Attorney, Agent, or Firm—Oblon, Spivak, McClelland, Maier & Neustadt, P.C.

(57) ABSTRACT

A process for separating mixtures of hydrocarbon isomers on molecular sieves, including providing columns which include molecular sieves and function alternatively as secondary adsorption, primary adsorption, and desorption devices, feeding the mixtures of hydrocarbon isomers to a column functioning as the primary adsorption device for adsorbing isomers with greater selectivity towards the molecular sieves, feeding effluent of the mixtures from the column functioning as the primary adsorption device to a column functioning as the secondary adsorption device for adsorbing remaining isomers with greater selectivity, discharging isomers with a lower selectivity from the column functioning as the secondary adsorption device and a desorbing agent therein, feeding a desorbing agent to the column functioning as the desorption device, discharging isomers with a greater selectivity towards the molecular sieves and the desorbing agent in the column functioning as the desorption device.

12 Claims, 2 Drawing Sheets

PROCESS FOR SEPARATING MIXTURES OF HYDROCARBON ISOMERS IN GAS PHASE ON MOLECULAR SIEVES

BACKGROUND OF THE INVENTION

1. Field of the Invention

The present invention relates to a process for separating mixtures of hydrocarbon isomers in gas phase on molecular sieves.

2. Discussion of the Background

The separation of the constituents of a mixture of hydrocarbon isomers, with very similar boiling points, is traditionally based on suitable technical combinations of super-fractionation and crystallization processes, with high costs and poor yields.

Alternatively, it is possible to obtain the separation of one or more isomers more economically and efficiently by means of adsorption processes on molecular sieves carried out in liquid phase (U.S. Pat. No. 3,917,734, U.S. Pat. No. 3,998,901); in these systems, the fluid and adsorbing solid are put in contact with each other in countercurrent. The movement of the solid can be either effective or simulated, the latter being effected by continuously varying the position of the feeds and sampling over a period of time.

For some hydrocarbon groups (paraffins-olefins, $C_4$–$C_5$ cuts), there are also processes on molecular sieves, carried out at such temperature and pressure values as to ensure a feeding mixture in vapor phase (U.S. Pat. No. 5,563,299).

These processes consist of two sections:

passage of the mixture on a fixed bed of molecular sieves where the isomers with a greater selectivity are withheld and the remaining ones are eluted (refined product);

recovery of the withheld isomers by desorption with a desorbing agent in vapor phase (extracted product). The continuous unit which effects this process therefore comprises the installation of at least two fixed molecular sieve beds (or multiples of two, i.e. 4, 6, 8, etc.) operating alternatively in adsorption and desorption.

This process is completed by distillation operations for the recovery of the refined product and extracted product from the desorbing agent; in fact it should be pointed out that the bed in adsorption phase comes from the previous desorption phase, at the end of which it is completely saturated with desorbing agent.

We have now found a process using the vapor phase with any mixture of hydrocarbon isomers which allows a greater recovery per cycle of the desired product in the refined product.

SUMMARY OF THE INVENTION

The process, object of the present invention, for separating mixtures of hydrocarbon isomers in gas phase on molecular sieves is characterized in that it comprises the following steps:

(a) feeding the mixtures of hydrocarbon isomers to a column, or several columns, an having the function of primary adsorption column, wherein part of the isomers with a greater selectivity towards the molecular sieves, are adsorbed;

(b) feeding the effluent from the primary adsorption column(s) to a column, or several columns, having the function of secondary adsorption column, wherein the remaining part of the isomers, with a greater selectivity towards the molecular sieves, are adsorbed, and from which a stream is discharged containing the isomers with a lower selectivity towards the molecular sieves and the desorbing agent already present in the column;

(c) feeding the desorbing agent to a column, or several columns, having the function of desorption column, from which a stream is discharged containing the isomers with a greater selectivity towards the molecular sieves and the desorbing agent itself;

(d) feeding the stream containing the isomers with a lower selectivity towards the molecular sieves and the desorbing agent, leaving the column (s) having the function of secondary adsorption column, to a distillation unit for the recovery of the desorbing agent to be recycled to the column(s) having a desorption function (e) feeding the stream containing the isomers with a greater selectivity towards the molecular sieves and the desorbing agent, leaving the column(s) having the function of desorption column, to another distillation unit for the recovery of the desorbing agent to be recycled to the column(s) having a desorption function, steps (a), (b) and (c) being effected by means of three phases and a number of three or a multiple of three columns having fixed molecular sieve beds, so that from one phase to another, these columns pass alternatively in sequence from secondary adsorption column functions, to primary adsorption column functions, to desorption column functions.

The adsorptions are preferably carried out at a temperature ranging from 20 to 180° C. and at a pressure ranging from 1 to 10 bars.

The desorbing agent used, selected on the basis of the mixtures of hydrocarbon isomers present, can be an aliphatic hydrocarbon (pentane, hexane, heptane, octane, etc.) in vapor phase or an aromatic hydrocarbon (benzene, toluene, metaxylene, etc.) again in vapor phase.

Any molecular sieve capable of having greater selectivity with respect to certain hydrocarbon isomers may be used in the process object of the present invention. In particular, molecular sieves of the zeolitic type (for example X and Y zeolites) can be used.

The process object of the invention is mainly recommended when there are mixtures of hydrocarbon isomers having a number of carbon atoms less than or equal to 10.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
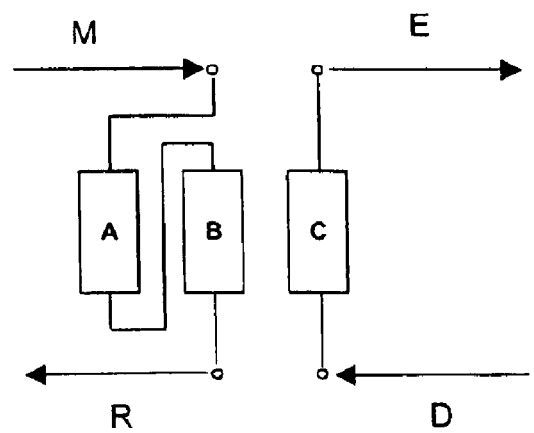
FIG. 1 is a schematic diagram of Phase 1 of an embodiment according to the present invention.
Figure 2:
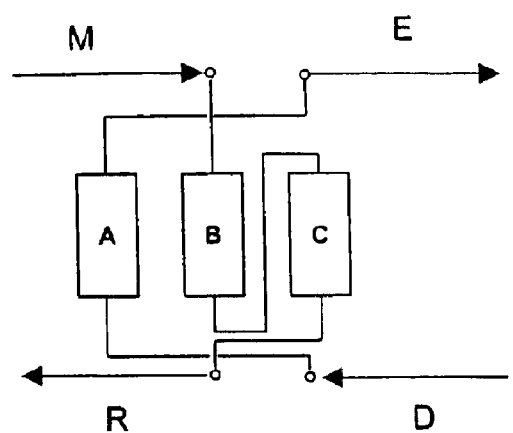
FIG. 2 is a schematic diagram of Phase 2 of the embodiment shown in FIG. 1.
Figure 3:
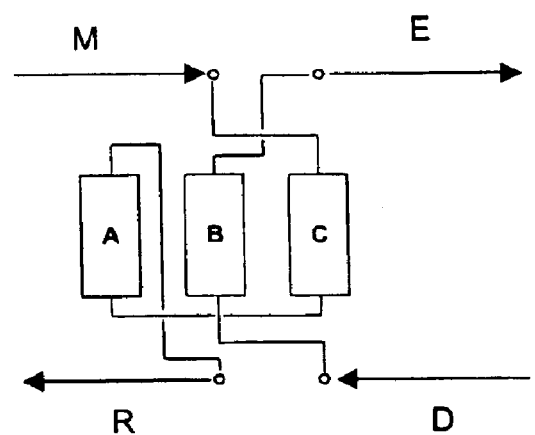
FIG. 3 is a schematic diagram of Phase 3 of the embodiment shown in FIGS. 1 and 2.

The invention is illustrated hereunder with the help of the schemes of FIGS. 1, 2 and 3, which represent an embodiment of the separation cycles consisting of three phases using three columns.

In phase 1, FIG. 1, the hydrocarbon mixture of isomers (M) is fed to the primary column (A), the effluent of which is in turn sent to the secondary column (B), from which a "Refined" stream (R) is obtained, consisting of components with a lesser affinity (selectivity) towards the molecular sieves, and the desorbing agent (Adsorption). A third column (C) is fed with the desorbing agent (D); the outgoing "Extract" stream (E) consists of components present in the feeding mixture having a greater affinity with the bed (adsorbed products), and the desorbing agent (Desorption).

In phase 2, FIG. 2, the hydrocarbon mixture is sent to the secondary column of the previous phase (B, now primary), whose effluent is fed to column C (which passes from desorption to secondary column); the primary column of the previous phase passes to desorption (A).

In phase 3, FIG. 3, the previous phase scheme is repeated so as to complete the cycle; the mixture is therefore fed to column C (primary), the refined product is collected by column A (secondary) and column B is in desorption.

Some illustrative but non-limiting examples are provided for a better understanding of the present invention.

EXAMPLE 1–4

Equilibrium tests: determination of the selectivities and vapor phase-liquid phase comparison.

The selectivity of a zeolite is defined as $$S_{ij} = (iwt\%/jwt\%)_{ADS} / (iwt\%/jwt\%)_{MIX}$$

(wherein ADS is the adsorbed phase and MIX is the gas phase)

and is determined under equilibrium conditions by means of experimental tests, carried out at a temperature of about 160° C. and about 1.1 bars, using a column having a diameter of 8.5 mm and a length of 55 mm, containing about 26 g of zeolite. The equilibrium condition is verified when the composition of the effluent mixture from the column is identical to that of the feeding mixture. The experimental test comprises an adsorption phase of the mixture up to equilibrium conditions, effected on a bed saturated with desorbing agent (Toluene) and a desorption phase, also carried out until equilibrium, the desorbing agent being fed in countercurrent. In both phases the stream leaving the column is collected and its composition is determined; the selectivities of the components and adsorbing capacity of the zeolite, defined as the adsorbed mass per unit of zeolite mass, are calculated on the basis of these analyses. The embodiment of the process in vapor phase has 2 advantages:

lower quantity of mixture fed (with a practically unaltered composition) which fills the dead volume of the zeolitic bed with respect to the process in liquid phase;

better selectivity values with respect to the corresponding values in liquid phase as indicated in Table 1 for 2 different zeolites, in the case of mixtures of $C_8$ isomers with an equimolecular composition.

The data of Comparative examples 1 and 3 in Table 1 were obtained from U.S. Pat. No. 3,917,734 and U.S. Pat. No. 3,998,901 respectively.

EXAMPLES 5–6

Separation tests: comparison of process with two and three columns.

The purpose of the separation tests is to establish the separation performances of a molecular sieve unit with respect to a mixture having a well defined composition; the laboratory unit used consists of 2 columns having the zeolite dimensions and charge described above, situated inside an oven to maintain the 160° C. required by the test.

The separation tests with 2 columns were carried out in continuous, i.e. always with an adsorption column and a desorption column, with recovery of both the refined and extracted product. The separation tests with 3 columns were effected, on the contrary, batchwise, i.e. alternating each adsorption phase, with both columns operating, and recovering the refined product, with a phase during which the extract is recovered and the column, which in the previous phase had the function of primary column, is desorbed. There is therefore a total of six phases per cycle, with respect to the 3 necessary when there are three columns available.

Table 2 indicates the separation performances for the two processes under examination, obtained with columns having the same dimensions and characteristics, feeding rev the same mixture (93% Etb, 7% Px) and with the same degree of purity as the refined product (Etb at 99.9%).

In the three-column process, the recovery of Etb, or in general of the desired product in the refined product, increases significantly; in the specific case it passes from 48% to 56%, with an increase of 16.7%. This variation, especially in cases in which the extract can be recycled to plant sections upstream of the molecular sieve unit, as illustrated in the block scheme of FIG. 4, allows a considerable reduction in the energy specification (energy necessary for producing a kg of refined product). In the case analyzed, in the passage from 2 to 3 columns, the energy specification of Ethylbenzene at 99.9% passes from 7020 kcal/kg to 6750 kcal/kg.

Figure 4:
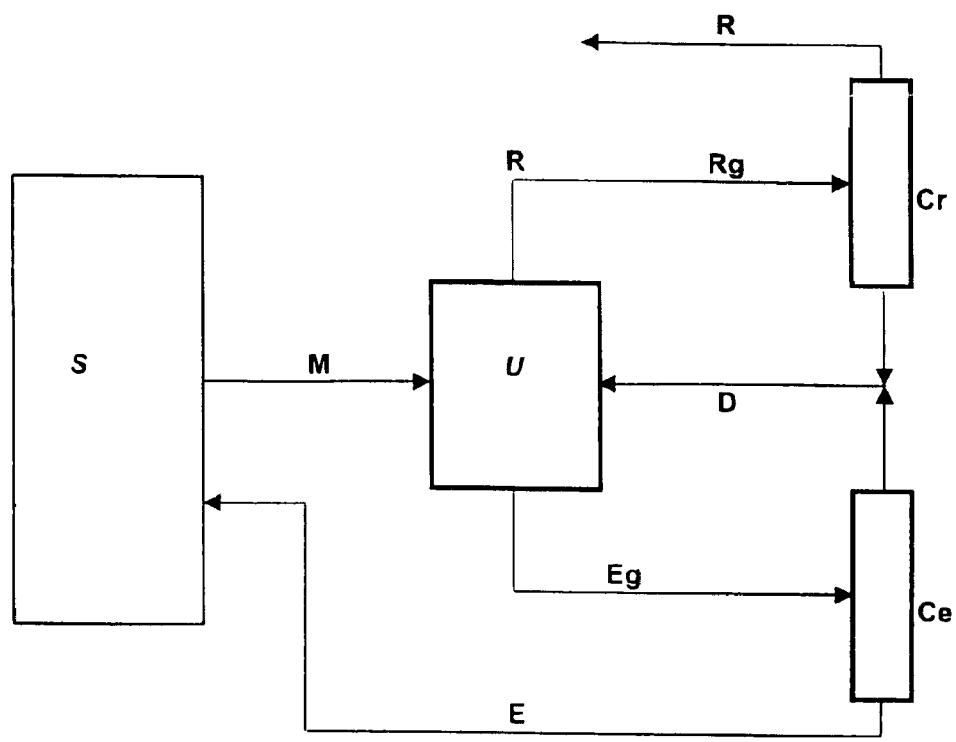
FIG. 4 is a schematic block diagram showing another embodiment according to the present invention.

The scheme of FIG. 4 illustrates:

(S): the plant section upstream of the molecular sieve unit;

(U): the molecular sieve separation unit;

($C_e$) the recovery column of the desorbing agent from the extract;

($C_f$): the recovery column of the desorbing agent from the refined product;

(M): the charge;

($R_c$): the refined product;

($E_c$): the extracted product;

($R_c$): the crude refined product, i.e. the refined product and the desorbing agent;

($E_c$) the crude extract, i.e. the extracted product and the desorbing agent;

(D): the desorbing agent.

TABLE I

| Ex. | Zeolite | Phase | Selectivity | | | | Adsorbing capacity |
|---|---|---|---|---|---|---|---|
| | | | Etb/Px | Px/Px | Mx/Px | Ox/Px | |
| 1 | 13-X-C | Liquid | 0.900 | 1.000 | 1.731 | 1.957 | — |
| 2 | 13-X-C | Vapor | 0.568 | 1.000 | 2.073 | 1.818 | 17.30% |
| 3 | 13-X-Sr | Liquid | 0.426 | 1.000 | 1.353 | 1.000 | — |
| 4 | 13-X-Sr | Vapor | 0.393 | 1.000 | 1.767 | 1.275 | 16.00% |

TABLE II

| Ex Columns | % Etb in feeding | % Etb in refined product | Phase time | Cycle time Cycle | Etb recovered | Des/Mix ratio |
|---|---|---|---|---|---|---|
| 5 Two | 93.0% | 99.9% | 1900 | 3800 | 48.0% | 2.5 |
| 6 Three | 93.0% | 99.9% | 2200 | 6600 | 56.0% | 2.6 |

What is claimed is:

1. A process for separating mixtures of hydrocarbon isomers in gas phase on molecular sieves, comprising the steps of:

providing a plurality of columns each including molecular sieves and configured to function alternately such that the columns are designated to function from a secondary adsorption device, to a primary adsorption device, and to a desorption device in sequence;

feeding the mixtures of hydrocarbon isomers to at least one of the columns functioning as the primary adsorption device such that isomers with a greater selectivity towards the molecular sieves in the mixtures of hydrocarbon isomers are adsorbed;

feeding an entire effluent of the mixtures of hydrocarbon isomers from the at least one of the columns functioning as the primary adsorption device to at least one of the columns functioning as the secondary adsorption device such that remaining of the isomers with a greater selectivity towards the molecular sieves are adsorbed;

discharging isomers with a lower selectivity towards the molecular sieves in the mixtures of hydrocarbon isomers from the at least one of the columns functioning as the secondary adsorption device and a desorbing agent remaining therein;

feeding a desorbing agent to at least one of the columns functioning as the desorption device;

discharging isomers with a greater selectivity towards the molecular sieves in the mixtures of hydrocarbon isomers and the desorbing agent in the at least one of the columns functioning as the desorption device;

feeding the isomers with a lower selectivity towards the molecular sieves and the desorbing agent discharged from the at least one column functioning as the secondary adsorption device to a first distillation unit configured to recover the desorbing agent for recycling for the at least one column functioning as the desorption device;

feeding the isomers with a greater selectivity towards the molecular sieves and the desorbing agent discharged from the at least one of the columns functioning as the desorption device to a second distillation unit configured to recover the desorbing agent for recycling for the at least one of the columns functioning as the desorption device; and rotating the columns from the secondary adsorption device, to the primary adsorption device, and to the desorption device in sequence, wherein at least the steps performing adsorption and desorption of the hydrocarbon isomers in gas phase are carried out at a pressure of about 1.1 bar.

2. The process according to claim 1, wherein the columns are configured to carry out at a temperature ranging from 20 to 180° C. and at a pressure ranging from 1 to 10 bars when functioning as the primary and secondary adsorption devices.

3. The process according to claim 1, wherein the desorbing agent is an aliphatic hydrocarbon in vapor phase or an aromatic hydrocarbon in vapor phase.

4. The process according to claim 1, wherein the hydrocarbon isomers have a number of carbon atoms less than or equal to 10.

5. The process according to claim 1, wherein the columns comprises at least three columns.

6. A process for separating mixtures of hydrocarbon isomers in gas phase on molecular sieves, comprising the steps of:

providing a plurality of columns each including molecular sieves and configured to function alternately such that the columns are designated to function from a secondary adsorption device, to a primary adsorption device, and to a desorption device in sequence;

feeding the mixtures of hydrocarbon isomers to at least one of the columns functioning as the primary adsorption device such that isomers with a greater selectivity towards the molecular sieves in the mixtures of hydrocarbon isomers are adsorbed;

feeding an entire effluent of the mixtures of hydrocarbon isomers from the at least one of the columns functioning as the primary adsorption device to at least one of the columns functioning as the secondary adsorption device such that remaining of the isomers with a greater selectivity towards the molecular sieves are adsorbed;

discharging isomers with a lower selectivity towards the molecular sieves in the mixtures of hydrocarbon isomers from the at least one of the columns functioning as the secondary adsorption device and a desorbing agent remaining therein;

feeding a desorbing agent to at least one of the columns functioning as the desorption device;

discharging isomers with a greater selectivity towards the molecular sieves in the mixtures of hydrocarbon isomers and the desorbing agent in the at least one of the columns functioning as the desorption device; and rotating the columns from the secondary adsorption device, to the primary adsorption device, and to the desorption device in sequence, wherein at least the steps performing adsorption and desorption of the hydrocarbon isomers in gas phase are carried out at a pressure of about 1.1 bar.

7. The process according to claim 6, further comprising feeding the isomers with a lower selectivity towards the molecular sieves and the desorbing agent discharged from the at least one column functioning as the secondary adsorption device to a first distillation unit configured to recover the desorbing agent for recycling for the at least one column functioning as the desorption device.

8. The process according to claim 6, further comprising feeding the isomers with a greater selectivity towards the molecular sieves and the desorbing agent discharged from the at least one of the columns functioning as the desorption device to a second distillation unit configured to recover the desorbing agent for recycling for the at least one of the columns functioning as the desorption device.

9. The process according to claim 6, wherein the columns are configured to carry out at a temperature ranging from 20 to 180° C. when functioning as the primary and secondary adsorption devices.

10. The process according to claim 6, wherein the desorbing agent is an aliphatic hydrocarbon in vapor phase or an aromatic hydrocarbon in vapor phase.

11. The process according to claim 6, wherein the hydrocarbon isomers have a number of carbon atoms less than or equal to 10.

12. The process according to claim 6, wherein the columns comprises at least three columns.

* * * * *